(12) United States Patent
Schulz et al.

(10) Patent No.: US 7,516,652 B2
(45) Date of Patent: Apr. 14, 2009

(54) METHOD AND DEVICE FOR EXCITING PRESSURE FLUCTUATIONS IN A FUEL SUPPLY SYSTEM OF AN INTERNAL COMBUSTION ENGINE

(75) Inventors: Oliver Schulz, Stuttgart (DE); Oliver Becker, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 38 days.

(21) Appl. No.: 11/290,284

(22) Filed: Nov. 29, 2005

(65) Prior Publication Data

US 2006/0144131 A1   Jul. 6, 2006

(30) Foreign Application Priority Data

Dec. 1, 2004 (DE) .................. 10 2004 057 963

(51) Int. Cl.
*G01M 19/00* (2006.01)
(52) U.S. Cl. .................. 73/114.43; 73/114.38
(58) Field of Classification Search ............... 73/117.2, 73/117.3, 118.1, 119 A, 114.38, 114.43
See application file for complete search history.

(56) References Cited

U.S. PATENT DOCUMENTS

| | | | | |
|---|---|---|---|---|
| 5,848,583 A | * | 12/1998 | Smith et al. | 123/497 |
| 6,138,638 A | * | 10/2000 | Morikawa | 123/295 |
| 6,311,669 B1 | * | 11/2001 | Przymusinski et al. | 123/300 |
| 7,110,875 B2 | * | 9/2006 | Fritsch et al. | 701/104 |
| 7,210,458 B2 | * | 5/2007 | Walther et al. | 123/446 |
| 2005/0049777 A1 | * | 3/2005 | Fritsch et al. | 701/104 |
| 2006/0130569 A1 | * | 6/2006 | Walther et al. | 73/119 A |

* cited by examiner

*Primary Examiner*—Harshad Patel
*Assistant Examiner*—Freddie Kirkland, III
(74) *Attorney, Agent, or Firm*—Kenyon & Kenyon LLP

(57) ABSTRACT

A method and a device for exciting pressure fluctuations in a fuel supply system of an internal combustion engine are provided, which in turn enable a determination of the sound velocity of the fuel. A quantity that characterizes the pressure in a fuel storage device or a fuel line is evaluated. In at least one operating state of the internal combustion engine, a natural oscillation of the fuel in the fuel storage device or the fuel line is excited.

18 Claims, 2 Drawing Sheets

METHOD AND DEVICE FOR EXCITING PRESSURE FLUCTUATIONS IN A FUEL SUPPLY SYSTEM OF AN INTERNAL COMBUSTION ENGINE

FIELD OF THE INVENTION

The present invention relates to a method and a device for exciting pressure fluctuations in a fuel supply system of an internal combustion engine.

BACKGROUND INFORMATION

It is known in the art that a fuel supply system of an internal combustion engine has at least one fuel storage device and at least one fuel line, a pressure being measured in at least one fuel storage device using a pressure sensor, and the pressure fluctuations being determined as a function of the measured pressure.

SUMMARY OF THE INVENTION

The method according to the present invention and the device according to the present invention for determining pressure fluctuations in a fuel supply system of an internal combustion engine provide the advantage that, in at least one operating state of the internal combustion engine, a natural oscillation (or self-oscillation) of the fuel in the fuel storage device or in the fuel line is excited. In this way, pressure fluctuations that can be evaluated may be achieved in the fuel storage device or in the fuel line, which in turn enable, for example, a reliable determination of the sound velocity of the fuel (i.e., velocity at which sound travels in the fuel) in the fuel storage device or in the fuel line. In general, properties of the fuel in the fuel storage device or in the fuel line, such as a natural (i.e., resonant or characteristic) frequency or a sound velocity of the fuel, can be determined easily and reliably.

It is especially advantageous that in the evaluation of the quantity that results when the natural oscillation is excited and which characterizes the pressure in the fuel storage device or in the fuel line, a sound velocity of the fuel in the fuel storage device or in the fuel line is determined.

In this way, pressure fluctuations of the fuel in the fuel storage device or in the fuel line can be reliably acquired, thus enabling an extensive compensation of their effects. The determination of the sound velocity of the fuel can also be determined in this way without using characteristic maps, and thus in a cost-effective manner.

It is particularly advantageous that from a temporal curve of the natural oscillation a frequency of the natural oscillation is determined, e.g., by a Fourier transform. In this way, the pressure fluctuations can be determined in a particularly simple and informative fashion. This frequency information can thus also be used for the compensation of the above-described pressure fluctuations.

A further advantage results if a sound velocity of the fuel is determined from the frequency of the natural oscillation, the length of the oscillation, and the order of the natural oscillation. In this way, the sound velocity of the fuel can be derived in a particularly simple and precise manner with the aid of mathematical relations.

A further advantage results if the natural oscillation is excited during working or driving operation of the internal combustion engine. In this way, the working or driving operation of the internal combustion engine need not be interrupted in order to excite the natural oscillation or, if necessary, to determine the sound velocity of the fuel.

It is also advantageous if the natural oscillation is excited during an overrun condition of the internal combustion engine. During an overrun condition, the supply of fuel to the fuel storage device or to the fuel line can be blocked without significantly adversely affecting the operation of the internal combustion engine. By blocking the fuel supply, the effects of disturbing quantities on the natural oscillation to be evaluated can largely be avoided, so that the determination of the sound velocity can take place even more reliably. In particular, when the fuel supply is blocked the pressure impacts induced by a fuel pump are no longer noticeable in the measured quantity that is characteristic for the pressure in the fuel storage device or in the fuel line, so that the curve of this quantity is much smoother. Due to the lower distortions in the measurement signal of the measured quantity, the sought natural frequencies in the Fourier spectrum can be detected in a more simple and precise fashion.

Therefore, it is particularly advantageous to excite the natural oscillation in the overrun condition with an interrupted fuel supply and/or an interrupted drawing off of fuel. This is because the interruption of the drawing off of fuel also avoids the superposition of disturbing pressure fluctuations, caused by the drawing off of fuel, on the temporal curve of the measured quantity in the fuel storage device or in the fuel line, so that the sought natural frequencies of the natural oscillation in the Fourier spectrum can likewise be detected more simply and more precisely due to the smaller disturbances in the measurement signal of the measured quantity.

A further advantage results if the sound velocity of the fuel is also determined dependent on a temperature of the fuel in the fuel storage device or in the fuel line. In this way, the sound velocity of the fuel can be determined more precisely. This advantage holds particularly true for an overrun operation, in which the fuel temperature decreases, especially since the sound velocity of the fuel is strongly dependent on the temperature of the fuel.

A further advantage results if the natural oscillation is excited by a brief opening of a pressure valve. In this way, a natural oscillation having a sufficiently large amplitude can be achieved in the fuel storage device or in the fuel line, which can also be resolved by a pressure sensor, for example.

In this context, it is particularly advantageous if the duration of opening of the pressure valve is less than or equal to the duration of the period of the anticipated natural oscillation. In this way, it is ensured that the desired natural oscillation can also be excited.

DETAILED DESCRIPTION

Figure 1:
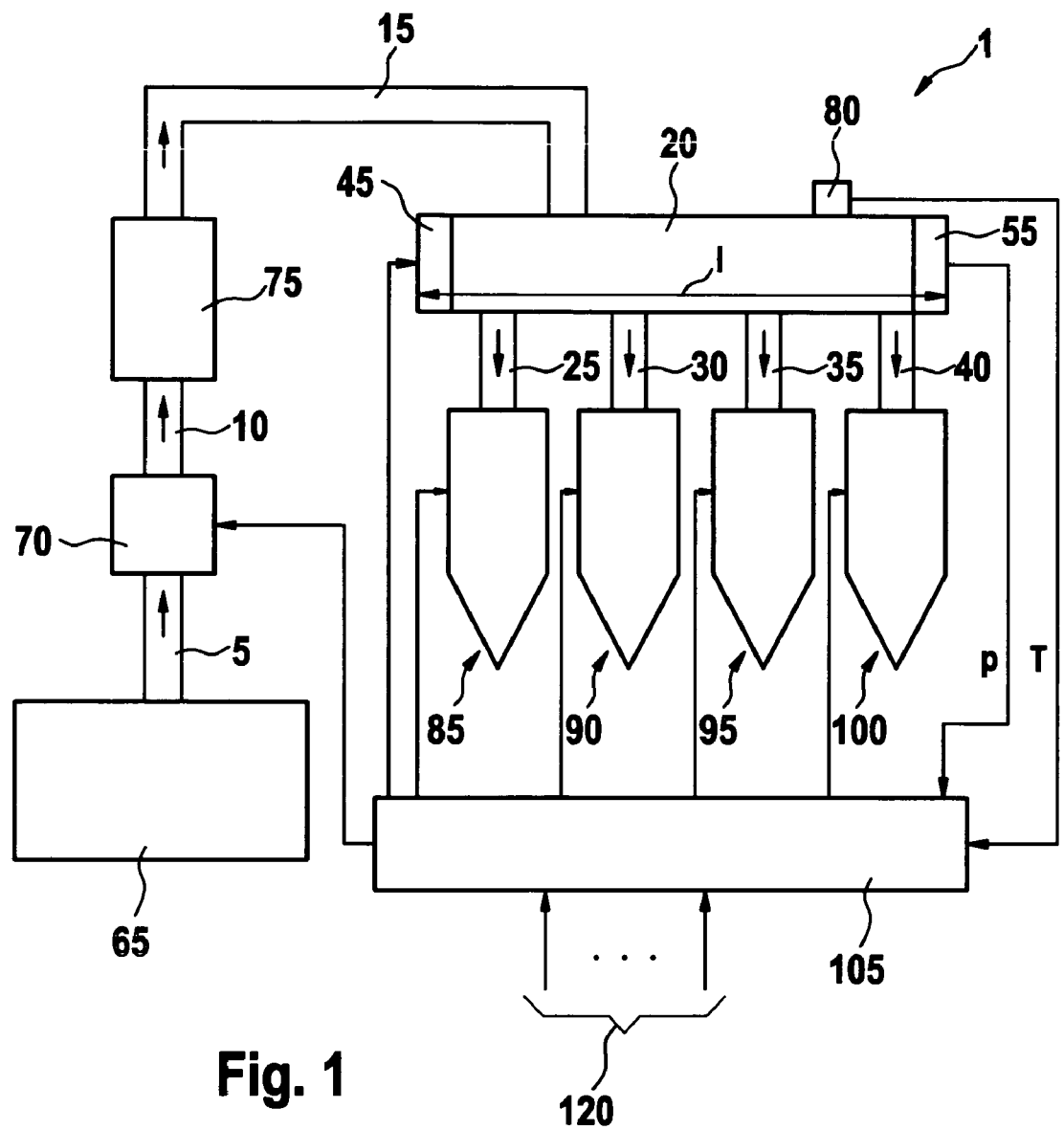
FIG. 1 shows a schematic illustration of a fuel supply system including the device according to the present invention.

In FIG. 1, 1 designates a fuel supply system of an internal combustion engine that drives a vehicle, for example. Here, fuel is pumped from a reservoir 65 by a vacuum pump (not shown in FIG. 1) into a fuel storage device 20 via a first fuel supply line 5, a fuel metering unit 70, a second fuel supply line 10, a high-pressure pump 75, and a third fuel supply line 15. Fuel metering unit 70 is controlled by a control unit 105, and controls the quantity of fuel suctioned by high-pressure pump 75. If the fuel metering unit is closed by control unit 105, high-pressure pump 75 no longer conveys fuel into fuel storage device 20, which is also referred to below as a fuel pressure storage device or a rail. High-pressure pump 75 can pump fuel into rail 20 only when fuel metering unit 70 is in the open state. Here, control unit 105 can control the suctioned quantity of fuel that high-pressure pump 75 can pump into rail 20 through the corresponding setting of a degree of opening of fuel metering unit 70. Fuel metering unit 70 can be, for example, fashioned in the form of a valve.

For injection into a combustion chamber of the internal combustion engine, the fuel situated in rail 20 can be supplied via a first high-pressure line 25 to a first injection valve 85, via a second high-pressure line 30 to a second injection valve 90, via a third high-pressure line 35 to a third injection valve 95, and via a fourth high-pressure line 40 to a fourth injection valve 100. The injection can take place directly into one or more cylinders of the internal combustion engine, or, alternatively, into an intake pipe of the internal combustion engine. The fuel can be injected directly into a cylinder via at least one of the injection valves. As an example, FIG. 1 shows four injection valves, but this number can also be greater or smaller. Injection valves 85, 90, 95, 100 are controlled by control unit 105 in order to set a predetermined opening time and opening duration, for example in order to realize the torque desired by the driver, as determined via an accelerator pedal, or in order to achieve a predetermined air/fuel mixture in the combustion chamber of the internal combustion engine.

In addition, a pressure valve 45, also called a pressure regulation valve in the following description, is situated in the area of rail 20. Pressure regulation valve 45 is controlled by control unit 105 in order to set a desired pressure of the fuel in rail 20. In addition, in the area of rail 20 there is situated a pressure sensor 55 that measures the fuel pressure in rail 20 and forwards a corresponding measurement signal to control unit 105. In addition, as shown in FIG. 1, a temperature sensor 80 can optionally be provided in the area of the rail, e.g., in an inner wall of the rail, that measures the temperature of the fuel in rail 20 and forwards a corresponding measurement signal to control unit 105. Additional input quantities supplied to control unit 105 are designated with reference character 120 in FIG. 1. These additional input quantities 120 can be, for example, an engine speed and a load on the internal combustion engine, and in particular an item of information concerning whether the internal combustion engine is in an overrun condition or in traction operation. From these additional input quantities 120, control unit 105 can determine an operating state of the internal combustion engine.

According to the present invention, it is provided in at least one operating state of the internal combustion engine to excite (or cause) a natural oscillation of the fuel in rail 20, and to measure the pressure that results in rail 20 when the natural oscillation has been excited, using pressure sensor 55. This measured pressure is then forwarded by pressure sensor 55 to control unit 105 in the form of the measurement signal. Because pressure sensor 55 continuously measures the fuel pressure in rail 20, in this way control unit 105 is continuously supplied with a temporal curve of the fuel pressure in rail 20 via the measurement signal.

Figure 2:
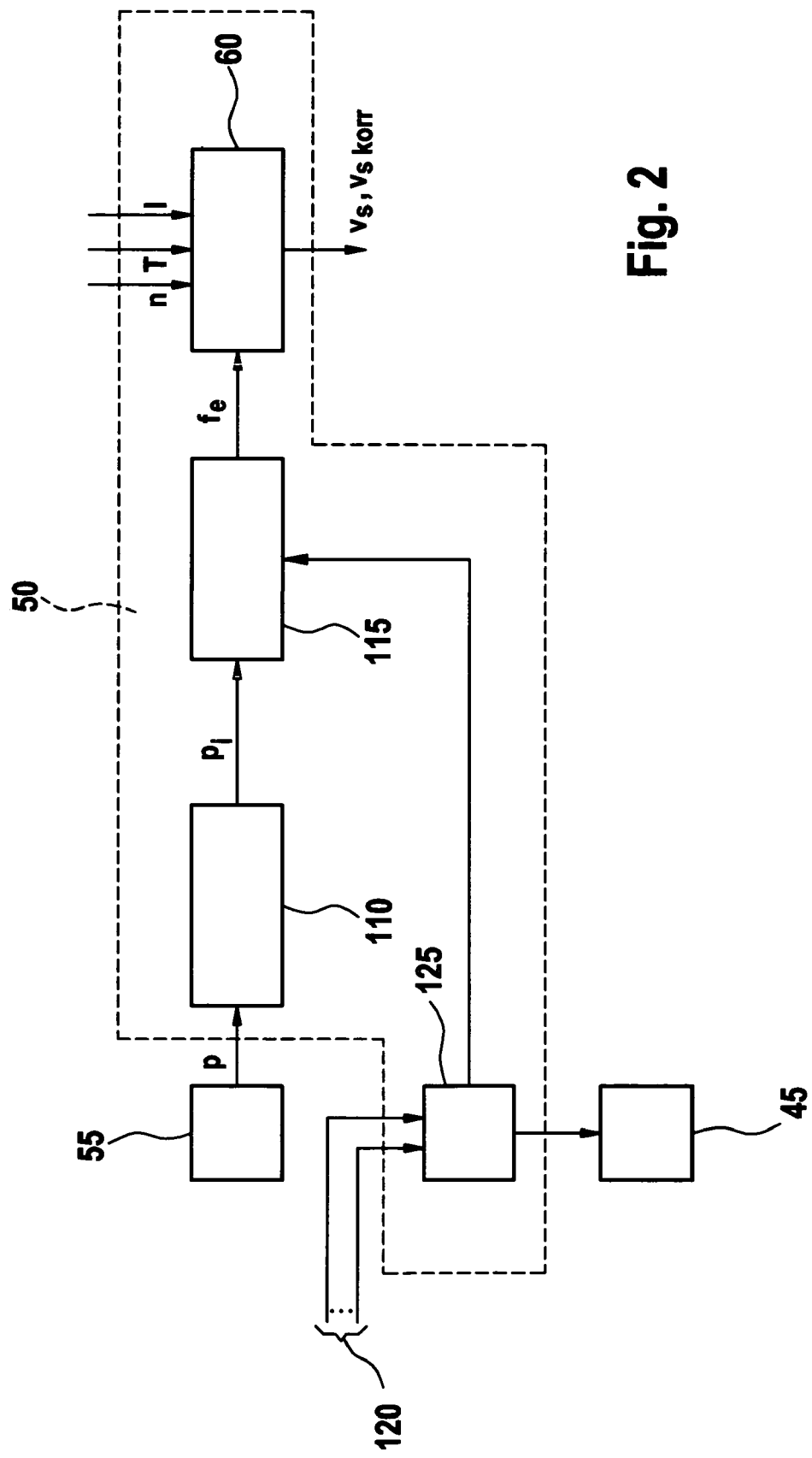
FIG. 2 shows a functional diagram illustrating the method and the device according to the present invention.

FIG. 2 shows a functional diagram that describes a device 50 according to the present invention, an on the basis of which diagram the method according to the present invention is also explained. Here, device 50 can be implemented in control unit 105 as software and/or as hardware. According to FIG. 2, device 50 includes a sampling unit 110 to which measurement signal p of pressure sensor 55 is supplied. Sampling unit 110 samples measurement signal p in order to provide at its output sampled values $p_i$ for a Fourier transform, which is carried out by a subsequent Fourier transform unit 115. The Fourier transform unit 115 then provides a natural frequency $f_e$ to a determining unit 60, to which are also supplied the length of rail 20, as the oscillation length, and the order of oscillation n of the developing natural oscillation having frequency $f_e$. From the oscillation frequencies supplied in the Fourier transform, the respectively allocated oscillation order n can be determined.

In addition, and optionally, determining unit 60 can also be supplied with the fuel temperature T, determined by temperature sensor 80. In the following, it will at first be assumed that fuel temperature T is not taken into account. Determining unit 60 then determines a sound velocity $v_s$ of the fuel in rail 20 from the provided natural frequency $f_e$, oscillation order n, and oscillation length l, according to the following equation:

$$v_s = f_e * l * n/2 \tag{1}$$

If the pressure cannot be measured at the operating point of interest, but only at an adjacent point, a possible variation of fuel temperature T must be taken into account. To the extent that the dependency of the sound velocity on the temperature is stored in, for example, characteristic maps, extrapolation can take place from the measurement point to the operating point that is of interest. The sound velocity then need be corrected only if the operating point of interest and the measurement point are different. Otherwise, the temperature dependency of the sound velocity is taken into account directly and automatically in the pressure measurement. On the basis of equation (1), in this way the influence of fuel temperature T on sound velocity $v_s$ of the fuel can be taken into account. Here, the sound velocity $v_s$ determined using equation (1) is corrected, dependent on fuel temperature T, to yield a corrected sound velocity $v_{s\,korr}$, which is then outputted by determining unit 60 instead of sound velocity $v_s$. The characteristic maps can be, for example, determined on a test bench.

If fuel temperature T is not measured, it can nonetheless be taken into account if, for example, the temperature characteristic of the fuel in a particular operating state of the internal combustion engine is known. For example, in an overrun condition the fuel temperature T generally decreases, because less fuel is driven through pressure regulating valve 45, so that lower throttling losses result, and because less fuel has to be compressed by high-pressure pump 75. Because, as described above, the sound velocity of the fuel is strongly dependent on fuel temperature T, the cooling of the fuel in rail 20 during the overrun condition must be taken into account. This can be accomplished either, as described, by measuring fuel temperature T or by parameterizing suitable characteristic maps in which the cooling characteristic is stored. These characteristic fields, which are, for example, also determined on a test bench, thus indicate which temperature the fuel has at a given time in the overrun condition. The fuel temperature T determined in this manner can then be used, for example, with the aid of a characteristic curve or a characteristic map, to correct the value for sound velocity $v_s$ determined using equation (1), in the manner described.

The sound velocity, determined in this way and corrected in temperature-dependent fashion if necessary, can then be supplied for further processing in control unit 105. The sound velocity of the fuel in rail 20 is an important quantity for some control functions in common-rail systems, which are, for example, constructed in the manner of the fuel supply system 1 according to FIG. 1. Thus, for example, the sound velocity is required for compensating pressure waves in rail 20 and in high-pressure lines 25, 30, 35, 40, i.e., for the correct compensation of the effects of pressure fluctuations in rail 20 and in high-pressure lines 25, 30, 35, 40. The sound velocity of the fuel is here dependent on the density and compressibility of the fuel; it is therefore a function of the type of fuel and the fuel temperature. While the fuel temperature can in principle be measured or modeled as described, it is currently not possible to detect the quality of fuel in the tank.

The only remaining problem is the question as to how a natural oscillation of the fuel can be excited in rail 20 for the reliable determination of natural frequency $f_e$, and thus also for the determination of the sound velocity of the fuel in rail 20. For this purpose, pressure fluctuations are to be induced in rail 20 that can be resolved by pressure sensor 55. Such an externally induced natural oscillation of the fuel in rail 20 can be, for example, initiated by a brief opening of pressure regulation valve 45. Here, the time constant of pressure regulation valve 45, i.e., the duration of time during which pressure regulation valve 45 is briefly open, should not be greater than the duration of the period of the anticipated natural oscillation that is to be detected. Because the natural oscillation of the fuel in rail 20 is in the range between approximately 700 and 1,000 Hz, pressure regulation valve 45 should have a time constant less than or equal to 2 ms. If the natural oscillation is triggered by the above-described brief, and not necessarily complete, opening of pressure regulation valve 45, there results a sufficiently large amplitude of the produced natural oscillation that is resolved by pressure sensor 55 and can thus be measured. Currently, conventional pressure sensors resolve approximately 2.5 bar. On the basis of a base rail pressure of the fuel provided by high-pressure pump 75 of, for example, approximately 400 bar, the oscillation amplitude is approximately 50 bar, and is thus easily able to be resolved by pressure sensor 55. The proposed base rail fuel pressure for current fuel supply systems of approximately 400 bar results from the assumption of a base value of approximately 300 bar for the reliable operation of the fuel supply system, in addition to approximately 50 bar for the production of the natural oscillation and another 50 bar for the oscillation itself.

The frequency of the natural oscillation, i.e., the natural frequency, is, to a first approximation (i.e., given isentropic conditions), independent of the amplitude of the natural oscillation. This is a typical property of linear systems, but does not necessarily hold for non-linear systems. Because the system under consideration here is linear to a first approximation, it does not matter which pressure irruption, or which amplitude of the natural oscillation, is produced by the brief opening of pressure regulation valve 45. The measured natural frequency $f_e$ will be approximately the same, independently of this. Thus, the demands made on the excited oscillation amplitude by pressure regulation valve 45 are low. Accordingly, if pressure regulation valve 45 is charged with the maximum allowable flow, no high demands will be made on the precision of the current strength, the duration of the flow, or the opening cross-section of pressure regulation valve 45. The decisive factor is that the dynamic behavior of pressure regulation valve 45 must be sufficient to excite the oscillation, i.e., the duration of opening of pressure regulation valve 45 can be kept sufficiently short, as described above. Thus, the degree to which pressure regulation valve 45 is opened during its brief opening is not critical.

The excitation of the natural oscillation can, for example, take place dependent on the presence of a particular operating state of the internal combustion engine supplied with fuel by fuel supply system 1. Device 50 includes an excitation unit 125 to which additional input quantities 120 are supplied, and that derives the operating state of the internal combustion engine from the additional input quantities 120. In particular, excitation unit 125 determines whether the internal combustion engine is in traction operation or in overrun operation. Excitation unit 125 compares the current operating state of the internal combustion engine, derived from the supplied additional input quantities 120, with an operating state of the internal combustion engine specified for the excitation of the natural oscillation in rail 20. If there is agreement, excitation unit 125 causes pressure regulation valve 45 to execute the above-described brief opening in order to excite the natural oscillation. Moreover, excitation unit 125 activates Fourier transform unit 115 in order to determine natural frequency $f_e$ from the temporal sequence of sampled values $p_i$. If there is a lack of agreement, no such controlling of pressure regulation valve 45 is carried out by excitation unit 125, and no activation of Fourier transform unit 115 by excitation unit 125 takes place. Thus, an evaluation of the temporal sequence of sampled values $p_i$ for the determination of natural frequency $f_e$ does not take place.

In the example according to FIG. 2, device 50 includes sampling unit 110, Fourier transform unit 115, determining unit 60, and excitation unit 125. Here, sampling unit 110, Fourier transform unit 115, and determining unit 60 are used to evaluate the temporal curve, acquired by pressure sensor 55, of pressure sensor p, and excitation unit 125 is used to excite the natural oscillation of the fuel in rail 20. Alternatively, device 50 can also include pressure sensor 55 and/or pressure regulation valve 45. In another alternative example embodiment, sampling unit 110 and/or Fourier transform unit 115 can be situated outside device 50, for example, combined with pressure sensor 55 in a common assembly. In the present example, it has been specified that excitation unit 125 activates Fourier transform unit 115 given the presence of the predetermined operating state of the internal combustion engine, and otherwise deactivates it. Alternatively, excitation unit 125 could correspondingly also activate and/or deactivate sampling unit 110 or determining unit 60.

For the excitation of the natural oscillation to be evaluated, traction operation of the internal combustion engine can be, for example, provided as a predetermined operating state that characterizes the working operation, or, in the case of the drive mechanism of a vehicle, the driving operation, of the internal combustion engine. Here, this operating state is allowed to excite the natural oscillation only if in this operating state brief, slight pressure fluctuations or oscillations of the fuel in rail 20 are permissible. Otherwise, an overrun condition of the internal combustion engine can be selected as the predetermined operating state for exciting the natural oscillation to be evaluated. As described above, in general the fuel temperature decreases in overrun conditions, so that in this case the temperature T of the fuel is to be taken into account in the above-described manner in determining the sound velocity of the fuel in rail 20, in order to obtain as reliable a value as possible for this sound velocity. Otherwise, the determined value for the sound velocity will have a corresponding error.

In overrun operation of the internal combustion engine, the closing of fuel metering unit 70 suggests itself as a way of exciting the natural oscillation. For this purpose, fuel metering unit 70 is controlled in a corresponding manner by control device 105, in particular by excitation unit 125 of device 50, when this unit recognizes that a overrun operation of the internal combustion engine predetermined for the excitation of the natural oscillation is currently present. In a corresponding manner, the injection via injection valves 85, 90, 95, 100 can be interrupted, these valves being controlled by control unit 105 or by excitation unit 125 in a corresponding manner when the overrun operation of the internal combustion engine specified for the excitation of the natural oscillation is present and has been recognized by excitation unit 125 via the additional input signals 120. High-pressure pump 75 now no longer pumps fuel into rail 20, because fuel metering unit 70 is closed. Rail 20 now represents a closed system, because fuel does not flow to it via third fuel supply line 15, and fuel also does not flow away from it via one of the high-pressure lines 25, 30, 35, 40. Now, by briefly opening pressure regulation valve 45, the natural oscillation can be excited by excitation unit 125. In pressure signal p, measured by pressure sensor 55 for this excited natural oscillation, the pressure impacts induced by the high-pressure pump or by the injection processes of injection valves 85, 90, 95, 100 now disappear, so that the pressure of the fuel in rail 20 runs much more smoothly over time. Due to the lower disturbances in pressure signal p, the sought natural frequency $f_e$ in the Fourier spectrum can be detected more simply and more precisely.

For the excitation of the natural oscillation in overrun operation, it can also be provided to excite only fuel metering unit 70 to interrupt the fuel supply, or to excite only injection valves 85, 90, 95, 100 to interrupt the drawing off of fuel; in each of these cases, only a part of the described disturbances of pressure signal p is then avoided. If only the supply of fuel is interrupted, the disturbances due to a pressure drop in rail 20 during fuel injection are not suppressed. If only the injection of fuel through injection valves 85, 90, 95, 100, i.e., the drawing off of fuel, is interrupted, then the disturbances in the measured pressure signal p resulting from the pressure impacts induced by the high-pressure pump are not suppressed. When the high-pressure pump is pumping and the injection is switched off, pressure regulation valve 45 will open after a short time in order to limit the pressure in rail 20. A complete suppression of the disturbances in pressure signal p can be achieved only by interrupting both the fuel supply, for example, by closing fuel metering unit 70, and also the drawing off of fuel, for example, by closing injection valves 85, 90, 95, 100.

Pressure signal p represents the temporal curve of the pressure of the fuel in rail 20, measured by pressure sensor 55. This temporal curve of the pressure is converted by sampling unit 110 into a temporal sequence of sampled values $p_i$. From this temporal sequence of sampled values $p_i$, Fourier transform unit 115 determines the frequency spectrum, and extracts therefrom the characteristic frequency $f_e$, for example, as the oscillation having the highest amplitude.

In the foregoing it has been described how a natural oscillation can be excited and evaluated in rail 20. In a corresponding manner, a natural oscillation of the fuel can be excited and evaluated in one of the fuel supply lines 5, 10, 15, or in one of the high-pressure lines 25, 30, 35, 40. For this purpose, corresponding fuel supply lines or high-pressure lines can be equipped with a corresponding valve and a corresponding pressure sensor, and optionally also with a corresponding temperature sensor. With the exception of first fuel supply line 5, in the remaining fuel supply lines 10, 15 and in high-pressure lines 25, 30, 35, 40, the supply of fuel can be interrupted by blocking fuel metering unit 70, and the drawing off of fuel can be interrupted by blocking injection valves 85, 90, 95, 100, so that in the manner described above, in particular in the overrun condition of the internal combustion engine, disturbances of the natural oscillation induced in the corresponding fuel supply line 10, 15 or in the corresponding high-pressure line 25, 30, 35, 40 can be avoided in the above-described manner. Thus, in the manner described above a sound velocity of the fuel can be determined in one of fuel supply lines 5, 10, 15 or in one of high-pressure lines 25, 30, 35, 40.

Instead of the pressure itself, in general a quantity characterizing the pressure can also be measured and evaluated. Here, the temporal curve of this quantity can be evaluated in the above-described manner by sampling and Fourier transform to its natural frequency, and the determination of the sound velocity can be determined in the above-described manner, based on the quantity that characterizes the pressure. In the example described above, the pressure itself was used as the quantity characterizing the pressure in order to determine the natural frequency $f_e$ and the sound velocity $v_s$ or the corrected sound velocity $v_{s\,korr}$. A quantity characterizing the pressure can also be, for example, a quantity formed in pressure sensor 55, e.g., the amplitude of a deflected pressure membrane, which is proportional to the pressure of the fuel in rail 20.

It is also possible to specify a plurality of operating states of the internal combustion engine for the excitation and evaluation of the natural oscillation, e.g., both traction operation and also overrun operation of the internal combustion engine.

The fuel used can be, for example, diesel fuel or gasoline.

What is claimed is:

1. A method for exciting pressure fluctuations in a fuel supply system of an internal combustion engine, the method comprising: in at least one operating state of the internal combustion engine, exciting a natural oscillation of the fuel in one of a fuel storage device and a fuel line by briefly opening a pressure valve for a duration when at least one of (i) a fuel supply to one of the fuel storage device and the fuel line is interrupted, and (ii) an injection of fuel is interrupted; and selecting the duration of the opening of the pressure valve to be less than or equal to a period duration of an expected natural oscillation.

2. The method of claim 1, further comprising:
evaluating a quantity that results when the natural oscillation has been excited and that characterizes a pressure in the one of the fuel storage device and the fuel line.

3. The method of claim 2, further comprising:
determining, in the evaluating, a sound velocity of the fuel in the one of the fuel storage device and the fuel line.

4. The method of claim 1, further comprising:
determining, from a curve over time of the natural oscillation, a frequency of the natural oscillation by using a Fourier transform.

5. The method of claim 4, further comprising:
determining a sound velocity of the fuel from the frequency of the natural oscillation, a length of the natural oscillation, and an order of the natural oscillation.

6. The method of claim 1, wherein the natural oscillation is excited in one of a working operation and a driving operation of the internal combustion engine.

7. The method of claim 1, wherein the natural oscillation is excited in an overrun condition of the internal combustion engine.

8. The method of claim 7, further comprising:
determining the sound velocity of the fuel as a function of a temperature of the fuel in the one of the fuel storage device and the fuel line.

9. The method of claim 1, wherein the natural oscillation is excited while interrupting at least one of a supply of the fuel and a drawing off of the fuel.

10. A device for exciting pressure fluctuations in a fuel supply system of an internal combustion engine, comprising:
an excitation arrangement to excite, in at least one operating state of the internal combustion engine, a natural oscillation of the fuel in one of a fuel storage device and a fuel line, wherein the excitation arrangement excites the natural oscillation by briefly opening a pressure valve for a duration; and
a selecting arrangement to select the duration of the opening of the pressure valve to be less than or equal to a period duration of an expected natural oscillation.

11. The device of claim 10, wherein a quantity is evaluated that results when the natural oscillation has been excited and that characterizes a pressure in the one of the fuel storage device and the fuel line.

12. The device of claim 11, wherein, in the evaluating, a sound velocity of the fuel in the one of the fuel storage device and the fuel line is determined.

13. The device of claim 10, wherein, from a curve over time of the natural oscillation, a frequency of the natural oscillation is determined by using a Fourier transform.

14. The device of claim 13, further comprising:
determining a sound velocity of the fuel from the frequency of the natural oscillation, a length of the natural oscillation, and an order of the natural oscillation.

15. The device of claim 10, wherein the natural oscillation is excited in one of a working operation and a driving operation of the internal combustion engine.

16. The device of claim 10, wherein the natural oscillation is excited in an overrun condition of the internal combustion engine.

17. The device of claim 16, wherein the sound velocity of the fuel is determined as a function of a temperature of the fuel in the one of the fuel storage device and the fuel line.

18. The device of claim 10, wherein the natural oscillation is excited while interrupting at least one of a supply of the fuel and a drawing off of the fuel.

\* \* \* \* \*